United States Patent [19]
Taskovich et al.

[11] Patent Number: 5,686,097
[45] Date of Patent: Nov. 11, 1997

[54] MONOGLYCERIDE/LACTATE ESTER PERMEATION ENHANCER FOR CODELIVERY OF STEROIDS

[75] Inventors: Lina Tormen Taskovich, Palo Alto; Su Il Yum, Los Altos; Nieves Marzan Crisologo, Sunnyvale, all of Calif.

[73] Assignee: Alza Corporation, Palo Alto, Calif.

[21] Appl. No.: 401,593

[22] Filed: Mar. 9, 1995

Related U.S. Application Data

[63] Continuation-in-part of Ser. No. 129,494, Sep. 29, 1993, abandoned.

[51] Int. Cl.⁶ ............................................. A61F 13/02
[52] U.S. Cl. ................... 424/448; 424/447; 424/449; 514/946
[58] Field of Search ......................... 424/447, 448, 424/449; 514/946

[56] References Cited

U.S. PATENT DOCUMENTS

| | | | |
|---|---|---|---|
| 3,527,864 | 9/1970 | MacMillan et al. | 424/177 |
| 3,896,238 | 7/1975 | Smith | 424/358 |
| 3,903,256 | 9/1975 | MacMillan et al. | 424/59 |
| 3,952,099 | 4/1976 | Smith | 424/227 |
| 4,046,886 | 9/1977 | Smith | 424/227 |
| 4,144,317 | 3/1979 | Higuchi et al. | 424/21 |
| 4,913,905 | 4/1990 | Fankhauser | 424/449 |
| 5,041,437 | 8/1991 | Yoshida et al. | 514/218 |
| 5,059,427 | 10/1991 | Yoshida et al. | 424/449 |
| 5,108,995 | 4/1992 | Casper | 514/170 |
| 5,211,952 | 5/1993 | Spicer et al. | 424/426 |
| 5,246,949 | 9/1993 | Yoshida et al. | 514/356 |
| 5,252,588 | 10/1993 | Azuma et al. | 514/317 |
| 5,256,421 | 10/1993 | Casper | 424/449 |
| 5,276,022 | 1/1994 | Casper | 514/170 |
| 5,314,694 | 5/1994 | Gale | 424/448 |

FOREIGN PATENT DOCUMENTS

| | | | |
|---|---|---|---|
| 0295411 | 12/1988 | European Pat. Off. | 31/445 |
| 0368339 | 5/1990 | European Pat. Off. | 31/505 |
| 9220377 | 11/1992 | WIPO | 47/14 |

*Primary Examiner*—J. Gabrielle Phelan
*Attorney, Agent, or Firm*—Michael J. Rafa; Steven F. Stone

[57] ABSTRACT

A composition of matter for application to a body surface or membrane to coadminister an estrogen and progesterone by permeation through the body surface or membrane, the composition comprising, in combination, the estrogen and progesterone to be administered, in a therapeutically effective amount; and a permeation-enhancing mixture comprising a monoglyceride or a mixture of monoglycerides, and a lactate ester or a mixture of lactate esters at specific concentrations. The composition of matter is used to provide hormone replacement therapy to a woman.

31 Claims, 6 Drawing Sheets

5,686,097

MONOGLYCERIDE/LACTATE ESTER PERMEATION ENHANCER FOR CODELIVERY OF STEROIDS

RELATED APPLICATIONS

This is a continuation-in-part of U.S. application Ser. No. 08/129,494, filed Sep. 29, 1993, now abandoned, which application is incorporated herein in its entirety by reference and benefit is claimed of its filing date.

FIELD OF THE INVENTION

This invention relates to the transdermal codelivery of drugs and other biologically active agents. More particularly, this invention relates to novel methods and compositions for enhancing the percutaneous coabsorption of steroids when incorporated in transdermal drug delivery systems. More particularly, but without limitation thereto, this invention relates to the transdermal codelivery of steroids utilizing a permeation-enhancing mixture of a monoglyceride and a lactate ester. Still more particularly, but without limitation thereto, this invention relates to the transdermal codelivery of steroids such as estradiol and progesterone utilizing a permeation-enhancing mixture of a monoglyceride and a lactate ester, wherein the monoglyceride and lactate ester are present in the composition in specific weight percentages.

BACKGROUND OF THE INVENTION

The transdermal route of parenteral delivery of drugs provides many advantages over other administrative routes. Transdermal systems for delivering a wide variety of drugs or other beneficial agents are described in U.S. Pat. Nos. 3,598,122; 3,598,123; 3,731,683; 3,797,494; 4,031,894; 4,201,211; 4,286,592; 4,314,557; 4,379,454; 4,435,180; 4,559,222; 4,568,343; 4,573,995; 4,588,580; 4,645,502; 4,704,282; 4,788,062; 4,816,258; 4,849,226; 4,908,027; 4,943,435; and 5,004,610. The disclosures of the above patents are incorporated herein by reference.

Estrogen replacement therapy is warranted in menopausal women for several reasons. Estrogen replacement will relieve hot flushes and this relief of flushes and night sweats improves sleep patterns and contributes to the patient's general feeling of well-being. (See Campbell S., Whitehead M. I. Estrogen therapy and the menopausal syndrome. In Clinics in Obstetrics and Gynecology: Volume 4. The Menopause, Edited by R. B. Greenblatt, J. W. W. Studd, London, W. B. Saunders, 1977, pages 31–47; Erlik Y., Tataryn I. V., Meldrum D. R. et al. Association of waking episodes with menopausal hot flushes. JAMA 24:1741, 1981). Estrogen replacement protects against postmenopausal loss of calcium from the skeleton, especially from vertebral bodies, preventing crush fractures and loss of body height. (See Lindsay R., Hart D. M., Forrest, C. et al. Prevention of spinal osteoporosis in oophorectomized women. Lancet 2:1151,1980). Several studies have now reported that long-term estrogen therapy is also associated with a reduction in the incidence of classical osteoporotic fractures of the forearm and hip. (See Hutchinson, T. A., Polansky, S. M., Finestein, A. Post-menopausal estrogens protect against fractures of hip and distal radius. Lancet 2:706, 1979; Paganini-Hill, A., Ross, R. K., Gerkins, V. R., et al. A case control study of menopausal estrogen therapy in hip fractures. Annals of Internal Medicine 95:28, 1981; Weiss N. S., Ure C. L, Ballard J. H. et al. Decreased risk of fractures of the hip and lower forearm with postmenopausal use of estrogen. New England Journal of Medicine 303:1195, 1980). Another beneficial effect of long-term estrogen use is the reduction of the risk of death from ischemic heart disease probably mediated by changes in blood lipoprotein concentrations. (See Ross R. K., Paganini-Hill A., Mack T. M. et al. Menopausal estrogen therapy and protection from ischemic heart disease. Lancet 1:858, 1981). Estrogen replacement has also been shown to improve the vascularity and health of the vaginal mucosa and urinary tract. The only major risk factor associated with estrogen administration in the doses required to relieve menopausal symptoms, is hyperstimulation of the endometrium and an increased risk of endometrial cancer. (See Cramer D. W., Knapp R. C. Review of epidemiologic studies of endometrial cancer and exogenous estrogen. Obstetrics and Gynecology 54:521, 1979; Shapiro S., Coughman D. W., Sloan D., et al. Recent and past use of conjugated estrogens in relation to adenocarcinoma of the endometrium. New England Journal of Medicine 303:485, 1980).

Estrogens predispose the endometrium to cancer by stimulating cell mitosis and proliferation and increasing the levels of DNA synthesis and nuclear estradiol receptors in the endometrium. (See Whitehead M. I., Townsen P. T., Pryce-Davies J., et al. Effects of estrogens and progestins on the biochemistry and morphology of the postmenopausal endometrium. New England Journal of Medicine 305:1599, 1981; Whitehead M. I., Townsen P. T., Pryce-Davies J., et al. Actions of progestins on the morphology and biochemistry of the endometrium of postmenopausal women receiving low dose estrogen therapy. American Journal of Obstetrics and Gynecology, 142:791,1982).

In order to avoid the risks described above, especially the risk of carcinoma of the endometrium and the breast, therapeutic systems are now designed to contain both estrogens and progestogens as active ingredients, and while oral combination pills are known in the art, they also have been well documented for their problems such as inconvenience and side effects. Transdermal delivery of the steroids is an attempt to eliminate or reduce those problems. See, eg, U.S. Pat. Nos. 5,256,421; 5,108,995; 4,913,905; 5,276,022; 5,211,952; 4,816,258; 4,788,062; and 4,863,738.

There are many factors, however, which affect the suitability of an active agent for transdermal administration. These are discussed at length in Knepp et al, "Transdermal Drug Delivery: Problems and Possibilities," CRC Critical Reviews in Therapeutic Drug Carrier Systems, Vol. 4, Issue 1 (1987). When it is desired to deliver more than one active agent from a single transdermal delivery device, the problems associated with achieving a workable multi-drug transdermal device with any specific combination of drugs are even more complex and difficult and can often prove to be insurmountable.

Conventional dosage forms such as tablets or injections can administer a combination of two or more active agents, each at their appropriate dose, merely by appropriate selection of the amount of each agent included in the dosage form. In transdermal delivery devices, however, the total dosage of each agent is not established by the amount of each agent that is in the device. Instead, the total dosage of each agent is the product of its average transdermal administration rate (μg/hr) and the time over which the device is applied, and the average administration rate of an agent from a transdermal delivery device is determined primarily by a combination of factors other than the amount of the agent present in the device.

In order for a transdermal delivery device to be able to administer two or more agents from a common reservoir over the same period of time, the relative permeabilities of each of the agents through the skin and the components of the device must bear the same relationship as their relative dosage or administration rate. Thus, for example, if the dosage of each agent were the same, for example 15 µg/day, each agent would have to have the same overall permeability. If, however, one agent were to be delivered at a dosage of 20 µg/day and the other at 1 µg/day, the overall permeability of one would have to be 20 times greater than that of the other.

If the problems associated with obtaining the desired relative administration rates of the individual agents to the skin can be solved, other factors remain with which to be dealt. The agents individually, in combination with each other, or in combination with a permeation enhancer if required, must not cause undue irritation or sensitization when applied topically under occlusion. Materials which individually are not irritating or sensitizing may become so when presented to the skin in combination with each other.

Further, the skin has been recognized as the largest metabolizing organ of the body, larger even than the liver. See, A. Pannatier, et al, "The Skin as a Drug Metabolizing Organ," Drug Metabolism Reviews, Vol. 8, No. 2, pp 319–343 (1978). Skin can metabolize agents administered transdermally into inactive or potentially harmful metabolites. Thus, it is necessary that the rate at which each agent is metabolized by the skin and the metabolites produced do not prevent the safe and therapeutically effective transdermal administration of each agent into the bloodstream at the desired administration rate.

Assuming these obstacles can be overcome, it is also important that the agent binding capacity of the skin for each of the agents have the proper relationship. Before transdermal administration of an agent into the bloodstream can commence at a steady state rate, the capacity of the skin below the device to bind the agent must be saturated. The time required to achieve this steady state rate is known as the "lag time" and is a function of the rate at which the agent permeates into the skin and the binding capacity of the skin for that agent. In order for the lag time for both agents to be the same, there must be an inverse relationship between each agent's administration rate and the binding capacity of the skin for each agent.

In many instances, drugs which would appear to be ideal candidates for transdermal delivery are found to have such low permeability through intact skin that they cannot be delivered at therapeutically effective rates from reasonably sized systems. The situation becomes more complicated if permeation enhancers are required to increase the inherent permeability of the skin to one or more of the agents being delivered. Identifying a permeation enhancer that has the ability to selectively increase the permeation of the skin to only one agent or to relatively increase the permeability of the skin to two or more agents in the required relationship could often provide an insurmountable obstacle for any specific combination of agents.

In an effort to increase skin permeability, it has been proposed to pretreat the skin with various chemicals or to concurrently deliver the drug in the presence of a permeation enhancer. Various materials have been suggested for this purpose, as described in U.S. Pat. Nos. 3,472,931, 3,527, 864, 3,896,238, 3,903,256, 3,952,099, 4,046,886, 4,130,643, 4,130,667, 4,299,826, 4,335,115, 4,343,798, 4,379,454, 4,405,616 and 4,746,515, all of which are incorporated herein by reference; British Pat. No. 1,001,949; and Idson, Percutaneous Absorption, J. Pharm. Sci., vol. 64, No. b6, June 1975, pp 901–924 (particularly 919–921).

To be considered useful, a permeation enhancer should have the ability to enhance the permeability of the skin for at least one and preferably a significant number of drugs. More importantly, it should be able to enhance the skin permeability such that the drug delivery rate from a reasonably sized system (preferably 5–50 $cm^2$) is at therapeutic levels. Additionally, the enhancer, when applied to the skin surface, should be non-toxic, non-irritating on prolonged exposure and under occlusion, and non-sensitizing on repeated exposure. Preferably, it should be capable of delivering drugs without producing topical reactions, burning or tingling sensations.

The present invention greatly increases steroid permeability through the skin, and also reduces the lag time between application of the steroids to the skin and attainment of the desired therapeutic effect.

While it is known in the art to combine permeation enhancers, see, eg, European Patent Publication numbers 0295411 and 0368339, incorporated herein in their entirety by references, this invention utilizes a novel combination of a monoglyceride and a lactate ester. Further, the invention utilizes specific weight percentages of the novel components, the monoglyceride and lactate ester, ie, 15 to 25 wt % of monoglyceride and 8 to 25 wt % of lactic acid ester. The combined effect and, further, specific weight percentages, produces a significant and surprising improvement ie, more than an additive effect, over use of either a monoglyceride or a lactate ester alone, as well as over the combination of monoglyceride and lactate ester in specified weight percentages.

SUMMARY OF THE INVENTION

The present invention relates to improved compositions and methods for improving the penetration of the codelivery of estrogens and progestogens that produce little or no skin irritation and that are delivered in an amount sufficient to provide a therapeutic effect.

An aspect of the present invention is to provide codelivery of estrogen and progestogen transdermally at therapeutically effective rates from a system utilizing a permeation enhancer mixture of a monoglyceride and a lactate ester, wherein each enhancer is present in specific weight proportions.

Another aspect of the invention is to provide a transdermal therapeutic system that codelivers a therapeutically effective amount of an estrogen and progestogen and which utilizes a permeation enhancer mixture of a monoglyceride and a lactate ester that are both present in specific weight proportions.

Another aspect of the invention is to provide effective hormone replacement therapy to a woman by transdermally codelivering an estrogen and progestogen in combination with a permeation enhancer mixture of a monoglyceride and a lactate ester in specific weight proportions.

These aspects mentioned above, as well as others, have been demonstrated by the present invention, which provides a device and method for the transdermal coadministration of a therapeutically effective amount of an estrogen, preferably estradiol, and progestogen, preferably progesterone, together with a skin permeation-enhancing amount of a mixture of a monoglyceride and a lactate ester, each of the permeation enhancers present in specific concentrations.

The system of the invention comprises a carrier or matrix adapted to be placed in drug- and permeation-enhancing mixture-transmitting relation to the selected skin or other body site. The carrier or matrix contains sufficient amounts of the steroids and the permeation-enhancing mixture to continuously coadminister to the site, over a predetermined delivery period, both of the steroids, preferably estradiol and progesterone, in a therapeutically effective amount, and the permeation-enhancing mixture of a monoglyceride and a lactate ester, present in specific concentrations, ie, 15 to 25 wt % of monoglyceride and 8 to 25 wt % of a lactate ester, preferably 20 wt % monoglyceride and 12 wt % lactate ester in an amount effective to enhance the permeation of the drug to the skin.

As used herein, the term "transdermal" delivery or application refers to the delivery or application of agents by passage through skin, mucosa and/or other body surfaces by topical application or by iontophoresis.

As used herein, the term "therapeutically effective" amount or rate refers to the amount or rate of drug or active agent needed to effect the desired therapeutic result, ie, hormone replacement therapy.

As used herein, the term "monoglyceride" refers to glycerol monooleate, glycerol monolaurate and glycerol monolinoleate, or a mixture thereof. These compounds are generally available as a mixture of monoglycerides, with the mixture deriving its name from the monoglyceride present in the greatest amount. In a preferred embodiment of this invention, the permeation enhancer monoglyceride component is glycerol monolaurate.

As used herein, the term "glycerol monooleate" refers to glycerol monooleate itself or a mixture of glycerides wherein glycerol monooleate is present in the greatest amount.

As used herein, the term "glycerol monolaurate" refers to glycerol monolaurate itself or a mixture of glycerides wherein glycerol monolaurate is present in the greatest amount.

As used herein, the term "glycerol monolinoleate" refers to glycerol monolinoleate itself or a mixture of glycerides wherein glycerol monolinoleate is present in the greatest amount.

As used herein, the term "lactate ester" or "lactic ester of an alcohol" refers to ethyl lactate, lauryl lactate, myristyl lactate or cetyl lactate, or a mixture thereof. Preferably, the lactate ester is lauryl lactate or myristyl lactate or a mixture thereof.

As used herein, the term "substantial portion of the time period" means at least about 60% of the time period, preferably at least about 90% of the time period. Correlatively, the term "substantially constant" means a variation of less than about ±20%, preferably less than about ±10%, over a substantial portion of the time period.

As used herein, the term "permeation enhancing mixture" refers to a mixture comprising one or more lactate esters and one or more monoglycerides. The monoglyceride or mixture, preferably, glycerol monolaurate, is present in the range of about 15 to about 25 weight percent. The second component, ie, a lactic acid ester, eg, lauryl, myristyl, cetyl, ethyl, methyl or oleic acid, benzoic acid or lactic acid is present in the range of about 8 to about 25 weight percent. More preferably, the permeation enhancer mixture by weight comprises 20% monoglyceride and 12% lactic acid ester.

As used herein, the term "predetermined delivery period" or "extended time period" refers to the delivery of drug for a time period of from several hours to seven days or longer. Preferably, the time period is from 16 hours to 3 or 4 days.

As used herein, the term "permeation enhancing amount or rate" refers to the rate or amount that provides increased permeability of the application site to the drug.

The term "estrogen" includes both the natural 17β-estradiol and estrone and the semi-synthetic estrogen derivatives such as the esters of natural estrogen, such as estradiol-17β-enanthate, estradiol-17β-valerate, estradiol-3-benzoate, estradiol-17β-undecenoate, estradiol-16,17-hemisuccinate or estradiol-17β-cypionate; 17-alkylated estrogens, such as ethinyl estradiol, ethinyl estradiol-3-isopropylsulphonate, quinestrol, mestranol or methyl estradiol; and non-steroidal compounds having estrogen activity, such as diethylstilbestrol, dienestrol, clomifen, chlorotrianisen or cyclofenil. The drug formulation of the invention preferably contains 17β-estradiol as the estrogen.

The term "progestogen" includes both the natural and synthetic agents such as progesterone, gestodene, levonorgestrel, northisterine acetate, norethindrone acetate, methyl progesterone, etc.

BRIEF DESCRIPTION OF THE DRAWINGS

The invention will be described in further detail with reference to the accompanying drawings wherein.

DESCRIPTION OF THE INVENTION

Figure 1:
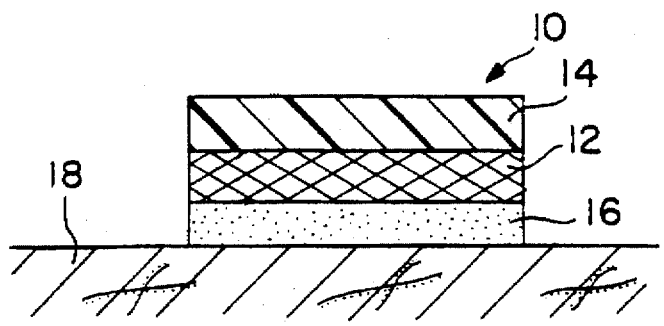
FIG. 1 is a cross-sectional view of one embodiment of the transdermal drug delivery system according to this invention.

This invention utilizes principles of transdermal drug delivery for effecting hormone replacement therapy by codelivering one or more monoglycerides and one or more lactate esters to aid in the delivery of an estrogen and progestogen across the skin. In addition, thereto this invention calls for the monoglycerides and lactate esters to be present in specific concentrations eg, 15–25 wt % and 8–25 wt %, respectively. The combined effect and preferred concentrations of the monoglycerides and lactate esters according to this invention have been shown to produce dramatic, ie, more than an additive, increases in the permeation of steroids when compared to the use of either a lactate ester or a monoglyceride alone or use of both components in unspecified weight percentages. Improved enhancement of permeation according to this invention can be obtained over a relatively wide range of lactate ester/monoglyceride weight percentages given above, however, the inventors have found that 20 wt % and 12 wt % of the monoglyceride and lactate ester, respectively, provides the greatest enhancement without any negative side effect.

The present invention in one embodiment is directed to a composition of matter for application to a body surface or membrane to administer at a therapeutically effective rate, an estrogen, preferably estradiol and a progestogen, ie, progesterone, by permeation through the body surface or membrane, the composition comprising, in combination:

(a) the estrogen and progestogen to be administered, in a therapeutically effective amount; and (b) a permeation-enhancing mixture comprising:

(i) 12 to 20 wt % of a monoglyceride or a mixture of monoglycerides, and (ii) 12 to 20 wt % of a lactate ester or a mixture of lactate esters.

The estrogen and progestogen may be present in the composition in an amount ranging from 0.6 to 5% and 10 to 15%, respectively by weight. The permeation-enhancing mixture preferably contains the monoglyceride and lactate ester in 20 wt % and 12 wt %, respectively.

This invention finds particular usefulness in enhancing the codelivery of estrogen and progestogen permeability at contraceptively effective rates across skin. It is also useful, however, in enhancing flux across mucosa. According to our invention, the permeation-enhancing mixture and the estrogen/progestogen mixture are placed in drug- and permeation-enhancing mixture-transmitting relationship to the appropriate body surface, preferably in a pharmaceutically acceptable carrier therefor, and maintained in place for the desired period of time.

The steroids and the permeation-enhancing mixture are typically dispersed within a physiologically compatible matrix or carrier as more fully described below, which may be applied directly to the body as an ointment, gel, cream, suppository or sublingual or buccal tablet, for example. When used in the form of a liquid, ointment, lotion, cream or gel applied directly to the skin, it is preferable, although not required, to occlude the site of administration. Such compositions can also contain other permeation enhancers, stabilizers, dyes, diluents, pigments, vehicles, inert fillers, excipients, gelling agents, vasoconstrictors, and other components of topical compositions as are known to the art.

In other embodiments, the drug and permeation enhancing mixture would be administered from a transdermal delivery device as more fully described below. Examples of suitable transdermal delivery devices are illustrated in FIGS. 1, 2, 3 and 4. In the drawings, the same reference numbers are used throughout the different figures to designate the same or similar components. The figures are not drawn to scale.

The reservoir matrix should be compatible with the drugs, the permeation enhancer and any carrier therefor. The term "matrix" as used herein refers to a well-mixed composite of ingredients fixed into shape.

In FIG. 1, transdermal delivery device 10 comprises a reservoir 12 containing the steroids, estrogen and progesterone, and the permeation-enhancing mixture. Reservoir 12 is preferably in the form of a matrix containing the drug and permeation enhancing mixture dispersed therein. Reservoir 12 is sandwiched between a backing layer 14 and an in-line contact adhesive layer 16. The device 10 adheres to the surface of the skin 18 by means of the adhesive layer 16. The adhesive layer 16 may optionally contain the permeation enhancing mixture and/or drug. A strippable release liner (not shown in FIG. 1) is normally provided along the exposed surface of adhesive layer 16 and is removed prior to application of device 10 to the skin 18. Optionally, a rate-controlling membrane (not shown) may be present between the reservoir 12 and the adhesive layer 16.

Figure 2:
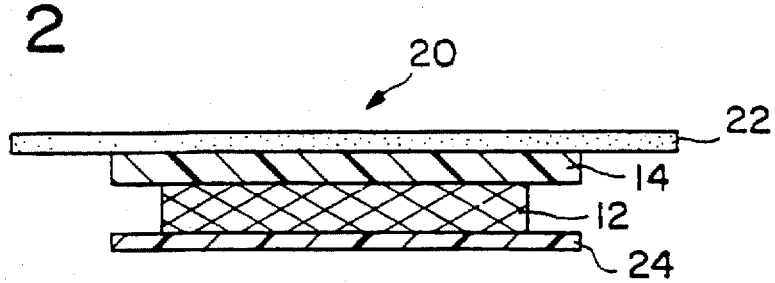
FIG. 2 is a cross-sectional view of another embodiment of the transdermal drug delivery system of this invention.

Alternatively, as shown in FIG. 2, transdermal therapeutic device 20 may be attached to the skin or mucosa of a patient by means of an adhesive overlay 22. Device 20 is comprised of a drug- and permeation enhancing mixture-containing reservoir 12 which is preferably in the form of a matrix containing the drug or drugs and the enhancing mixture dispersed therein. A backing layer 14 is provided adjacent on the surface of reservoir 12. Adhesive overlay 22 maintains the device on the skin or mucosa and may be fabricated together with, or provided separately from, the remaining elements of the device. With certain formulations, the adhesive overlay 22 may be preferable to the in-line contact adhesive 16 as shown in FIG. 1. Backing layer 14 is preferably slightly larger than reservoir 12, and in this manner prevents the materials in reservoir 12 from adversely interacting with the adhesive in overlay 22. Optionally, a rate-controlling membrane (not shown in FIG. 2) may be provided on the skin-proximal side of reservoir 12. A strippable release liner 24 is also provided with device 20 and is removed just prior to application of device 20 to the skin.

Figure 3:
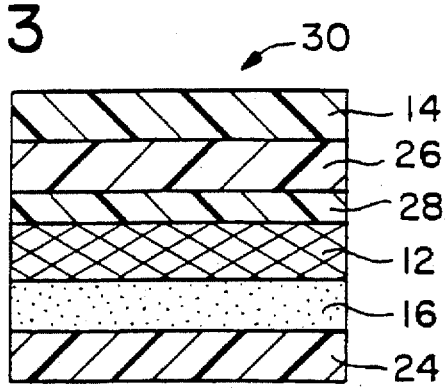
FIG. 3 is a cross-sectional view of still another embodiment of the transdermal drug delivery system according to this invention.

In FIG. 3, transdermal delivery device 30 comprises a drug- and permeation enhancing mixture-containing reservoir ("drug reservoir") 12 substantially as described with respect to FIG. 1. Permeation enhancer reservoir ("enhancer reservoir") 26 comprises the permeation enhancing mixture dispersed throughout and the drug or drugs at or below saturation when in equilibrium. Enhancer reservoir 26 is preferably made from substantially the same matrix as is used to form drug reservoir 12. A rate-controlling membrane 28 for controlling the release rate of the permeation enhancer from enhancer reservoir 26 to drug reservoir 12 is placed between the two reservoirs. A rate-controlling membrane (not shown in FIG. 3) for controlling the release rate of the enhancer from drug reservoir 12 to the skin or mucosa may also optionally be utilized and would be present between adhesive layer 16 and reservoir 12.

The rate-controlling membrane may be fabricated from permeable, semipermeable or microporous materials which are known in the art to control the rate of agents into and out of delivery devices and having a permeability to the permeation enhancer lower than that of drug reservoir 12. Suitable materials include, but are not limited to, polyethylene, polyvinyl acetate, ethylene n-butyl acetate and ethylene vinyl acetate copolymers and microporous polyolefinic films such as high density polyethylene and microporous polypropylene.

Superimposed over the permeation enhancer reservoir 26 of device 30 is a backing 14. On the skin-proximal side of reservoir 12 are an adhesive layer 16 and a strippable liner 24 which would be removed prior to application of the device 30 to the skin.

In the embodiments of FIGS. 1, 2 and 3, the carrier or matrix material of the reservoirs has sufficient viscosity to maintain its shape without oozing or flowing. If, however, the matrix or carrier is a low-viscosity flowable material such as a liquid or a gel, the composition can be fully enclosed in a pouch or pocket, as known to the art from U.S.

Pat. No. 4,379,454 (noted above), for example, and as illustrated in FIG. 4. Device 40 shown in FIG. 4 comprises a backing member 14 which serves as a protective cover for the device, imparts structural support, and substantially keeps components in device 40 from escaping the device. Device 40 also includes reservoir 12 which contains the drug or drugs and permeation enhancing mixture and bears on its surface distant from backing member 14 a rate-controlling membrane 28 for controlling the release of drugs and/or permeation enhancing mixture from device 40. The outer edges of backing member 14 overlay the edges of reservoir 12 and are joined along the perimeter with the outer edges of the rate-controlling membrane 28 in a fluid-tight arrangement. This sealed reservoir may be effected by pressure, fusion, adhesion, an adhesive applied to the edges, or other methods known in the art. In this manner, reservoir 12 is contained wholly between backing member 14 and rate-controlling membrane 28. On the skin-proximal side of rate-controlling membrane 28 are an adhesive layer 16 and a strippable liner 24 which would be removed prior to application of the device 40 to the skin.

Figure 4:
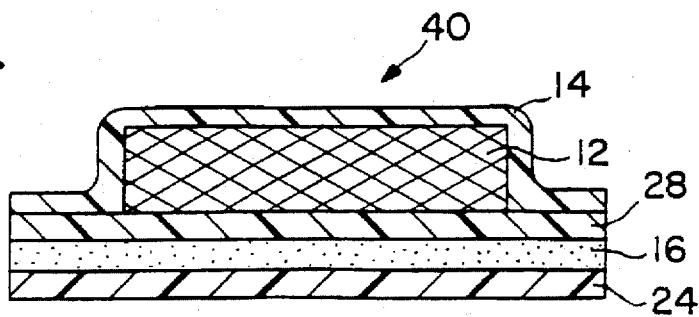
FIG. 4 is a cross-sectional view of yet another embodiment of the transdermal drug delivery system of this invention.

In an alternative embodiment of device 40 of FIG. 4, reservoir 12 contains the permeation enhancing mixture and the drugs at or below saturation. The drugs at saturation and an additional amount of permeation enhancing mixture are present in adhesive layer 16 which acts as a separate reservoir.

The drugs and the permeation enhancing mixture can be coextensively administered to human skin or mucosa by direct application to the skin or mucosa in the form of an ointment, gel, cream or lotion, for example, but are preferably administered from a skin patch or other known transdermal delivery device which contains a saturated or sub-saturated formulation of the drug and the enhancer. The formulation is non-aqueous based and designed to deliver the drug and the permeation enhancing mixture at the necessary fluxes. The suitability of a particular gel depends upon the compatibility of its constituents with both the drugs and the permeation enhancing mixture and any other components in the formulation.

When using a non-aqueous-based formulation, the reservoir matrix is preferably composed of a hydrophobic polymer. Suitable polymeric matrices are well known in the transdermal drug delivery art, and examples are listed in the above-named patents previously incorporated herein by reference. A typical laminated system would comprise a polymeric membrane and/or matrix such as ethylene vinyl acetate (EVA) copolymers, such as those described in U.S. Pat. No. 4,144,317, preferably having a vinyl acetate (VA) content in the range of from about 9% up to about 60% and more preferably about 9% to 40% VA.

It has also been found that matrices made from acetate-acrylate copolymer, give rise to unexpectedly high rates of drug delivery. These acetate-acrylate copolymer materials are available commercially. For example, Monsanto Chemical Company distributes a family of vinyl acetate-acrylate copolymer resin solutions under the trademarks GELVA® 737 and GELVA® 788 and Morton Tiokol, Inc. distributes acrylate copolymers under the trademarks Morstik 207A and Morstik 607.

These acrylate copolymer materials can be used separately or in mixtures. Several specific materials which have given rise to superior results are the Morstik 607 material, the GELVA® materials, which are believed to be based on 2-ethylhexyl acrylate, and mixtures of from about 20:1 to about 1:1 parts GELVA® 737 and GELVA® 788 (ratios given as weight ratios of GELVA® 737 to GELVA® 788).

All of these materials are solvent based but form films following casting and removal of the solvent. The term "solid" is used broadly since the "solid" product is generally a tacky, amorphous (ie, pressure sensitive adhesive) non-flowing material.

These materials are typically available as solutions in organic solvents such as toluene, ethanol, isopropanol, ethyl acetate and the like. These solvents are substantially eliminated from the matrix during fabrication.

These copolymers have the property of being high tack pressure sensitive adhesive when dried and/or cured. Thus, the matrices formed from these materials can adhere directly to the patient's skin without the need for additional separate adhesives.

The amount of drugs estradiol and progesterone that are present in the therapeutic device, and that are required to achieve a therapeutic effect, depend on many factors, such as the minimum necessary dosage of each of the drug; the solubility and permeability of the matrix, of the adhesive layer and of the rate-controlling membrane, if present; and the period of time for which the device will be fixed to the skin. The minimum amount of the drugs is determined by the requirement that sufficient quantities of drugs must be present in the device to maintain the desired rate of release over the given period of application. Generally the hormone replacement therapy of the present invention requires delivery of 50 micrograms of estradiol per day and about 2 mg of progesterone.

The estradiol and progesterone are normally present in the matrix or carrier at a concentration in excess of saturation, the amount of excess being a function of the desired length of the drug delivery period of the system. The drugs may, however, be present at a level below saturation without departing from this invention as long as the drugs are continuously administered to the skin or mucosal site in an amount and for a period of time sufficient to provide the desired therapeutic rate.

The permeation enhancing mixture is dispersed through the matrix or carrier, preferably at a concentration sufficient to provide permeation-enhancing amounts of enhancer in the reservoir throughout the anticipated administration period. Where there is an additional, separate permeation enhancer matrix layer as in FIGS. 3 and 4, the permeation enhancer normally is present in the separate reservoir. The concentration of permeation enhancer may be above or below saturation depending on the desired enhancement ratio.

The unexpected effects of the specific weight percentages of the components of the permeation enhancer mixture is due, in part to the solubility of the monoglyceride in the lactic acid ester. It is known that monoglycerides by themselves are effective permeation enhancers. The enhancement occurs by the solubilization of the monoglyceride in the drug reservoir. Thus, the solubilization of the monoglyceride in the drug reservoir increases as a function of lactic acid ester concentration. For example, the solubility of glycerol monolaurate in lauryl lactate is 350 mg/g of solution when the solution is stirred. GML is practically insoluble in, for example, an EVA 40 matrix. Thus, the amount of GML dissolved, ie, free GML is dictated by and proportional to the lauryl lactate loading in the polymer.

Based on the GML solubility of 350 mg/g, free GML concentrations based upon varying weight percents of lauryl lactate in EVA 40 are as follows:

| Wt % Lauryl Lactate | Wt % GML in Solution |
| --- | --- |
| 12% | 4.2% |
| 20% | 7.0% |
| 27% | 9.5% |
| 30% | 10.5% |

Thus, based upon the amount of GML in solution it would have appeared that the higher wt % of lauryl lactate would have resulted in a higher level of free GML and thus greater efficacy in increasing permeation. However, as shown by the examples, the preferred formulations, containing 20 wt % GML and 12 wt % lauryl lactate, were equally effective in enhancing drug permeability as those containing 20 wt % GML and 20 wt % lauryl lactate. While the invention is directed to a permeation enhancing mixture containing a monoglyceride or monoglyceride mixture from 12 to 20 wt % and a lactic acid ester present from 12 to 20 wt %, the 20 wt % monoglyceride and 12 wt % lactic acid ester is preferred because it is as effective as the higher percentage lactic acid ester compositions yet it contains less of a lactic acid ester which is a known potential irritant.

Examples of adhesives that may be used in the present invention are as follows: acrylate and pressure sensitive adhesives (eg, copolymers, graft, block-copolymers, radiation- or chemical crosslinked).

In addition to the drug mixture and the permeation enhancing mixture, which are essential to the invention, the matrix or carrier may also contain dyes, pigments, inert fillers, excipients and other conventional components of pharmaceutical products or transdermal devices known to the art.

Because of the wide variation in skin permeability from individual to individual and from site to site on the same body, it may be preferable that the drug mixture and the permeation enhancing mixture be administered from a rate-controlled transdermal delivery device. Rate control can be obtained either through a rate-controlling membrane or adhesive or both as well as through the other means.

Examples of rate-controlling membrane that can be used in the present invention are as follows: EVA and polyethylene films, polyurethane films microporous polypropylene, and microporous polyolefin films.

A certain amount of the drugs will bind reversibly to the skin, and it is accordingly preferred that the skin-contacting layer of the device include this amount of the agent as a loading dose.

The surface area of the device of this invention can vary from less than 1 cm² to greater than 200 cm². A typical device, however, will have a surface area within the range of about 5–50 cm².

The devices of this invention can be designed to effectively deliver drug for an extended time period of from several hours up to 7 days or longer. Seven days is generally the maximum time limit for application of a single device because the adverse effect of occlusion of a skin site increases with time and the normal cycle of sloughing and replacement of the skin cells occurs in about 7 days.

The method of this invention comprises:

(a) coadministering an estrogen and progestogen in a therapeutically effective amount, to an area of skin over a time period; and (b) coadministering the permeation-enhancing mixture according to this invention to the same area of skin.

The composition delivered by this method of the invention contains a permeation enhancing mixture, that is, 12 to 20 wt % or a monoglyceride or monoglyceride mixture and 12 to 20 wt % of a lactate ester and enough of each of the estrogen and progestogen to provide systemic administration of the drugs through the skin for a predetermined period of time to provide for effective hormone replacement therapy.

Preferably, a device for the transdermal coadministration of the estrogen and progesterone at a therapeutically effective rate, comprises:

(a) a reservoir comprising:

(i) an effective amount of an estrogen and progestogen, (ii) 12 to 20% by weight monoglyceride or mixture of monoglycerides, (iii) 12 to 20% by weight lactic acid ester, and (iv) the remainder ethylene vinyl acetate copolymer;

(b) a backing on the skin-distal surface of the reservoir; and (c) means for maintaining the reservoir in drug- and permeation enhancing mixture-transmitting relation with the skin.

Preferably, the estrogen is estradiol and the monoglyceride is glycerol monolaurate and the lactic acid ester is lauryl lactate.

More preferably, a device for the transdermal coadministration of the estrogen and progestogen, at a therapeutically effective rate, comprises:

(a) a reservoir comprising:

(i) 0.6 to 5% by weight estradiol, (ii) 10 to 15% by weight progesterone (iii) 20% by weight glycerol monolaurate, (iv) 12% by weight lauryl lactate, and (v) 48 to 57.4% by weight ethylene vinyl acetate copolymer;

(b) a backing on the skin-distal surface of the reservoir; and (c) means for maintaining the reservoir in drug- and permeation enhancing mixture-transmitting relation with the skin.

Preferably, the backing is a breathable backing, such as NRU-100-C® (Flexcon, Spencer, Mass.) or Sontara (Dupont, Wilmington, Del.). If an occluded backing is used, preferably it is Medpar® (3M, St. Paul, Minn.). Preferably, the means for maintaining the reservoir in drug and permeation enhancing mixture transmitting relation with the skin is an acrylic contact adhesive, such as MSP041991P, 3M. Preferably, the ethylene vinyl acetate copolymer has a acetate content of 33% or 40%.

The aforementioned patents describe a wide variety of materials which can be used for fabricating the various layers or components of the transdermal drug delivery devices according to this invention. This invention therefore contemplates the use of materials other than those specifically disclosed herein, including those which may hereafter become known to the art to be capable of performing the necessary functions. The following examples are offered to illustrate the present invention and are not intended to limit the invention in any manner.

EXAMPLE 1

The drug/permeation enhancer reservoir was prepared by mixing ethylene vinyl acetate copolymer having a vinyl acetate content of 40 percent ("EVA 40", U.S.I. Chemicals, Illinois) in an internal mixer (Bra Bender type mixer) until the EVA 40 pellets fused. Estradiol (Diosynth, Chicago, Ill.), progesterone (Upjohn, Grand Rapids, Mich.) glycerol monolaurate (Grinsted, Industrial Airport, Kansas) and lauryl lactate (Van Dyk, Inc., Belleview, N.J.) were then added. The mixture was blended for approximately 20 minutes at 40°–45° C. and 26 rpm. After blending, the mixture was calendered at 79°–81 ° C. to a 5 mil thick film. The film was then laminated to an acrylic contact adhesive (MSP-041991P, 3M) on one side and a pigmented Medpar® backing (3M, St. Paul, Minn.) on the opposite side. The laminate was then cut into circles using a stainless steel punch.

The composition of the drug reservoirs is shown in Table 1.

TABLE 1

| Drug/Permeation Enhancer Reservoir Composition (weight percent) |
| --- |
| progesterone/estradiol/glycerol monolaurate/lauryl lactate/EVA 40 (10/0.6/20/12/57.4) |
| progesterone/estradiol/glycerol monolaurate/lauryl lactate/EVA 40 (15/5/15/15/50) |
| progesterone/estradiol/glycerol monolaurate/lauryl lactate/EVA 40 (15/5/20/12/48) |

A circular piece of human epidermis was mounted on the recepteor compartment of a horizontal permeation cell with the stratum corneum facing the donor compartment of the cell. The release liner of the TTS system was then removed and the TTS system was centered over the stratum corneum side of the epidermis. An o-ring was put on top and the donor compartment of the cell was clamped together with the receptor compartment. A known volume of the receptor solution ie, water 1% Tween 20 in water, 2% propylene glycol in water or 2% IPA in water, that had been equilibrated at 35° C. was dispensed into in the receptor compartment. Air bubbles were removed from the receptor compartment; the cell was capped and placed in a water bath-shaker at 35° C.

Figure 5:
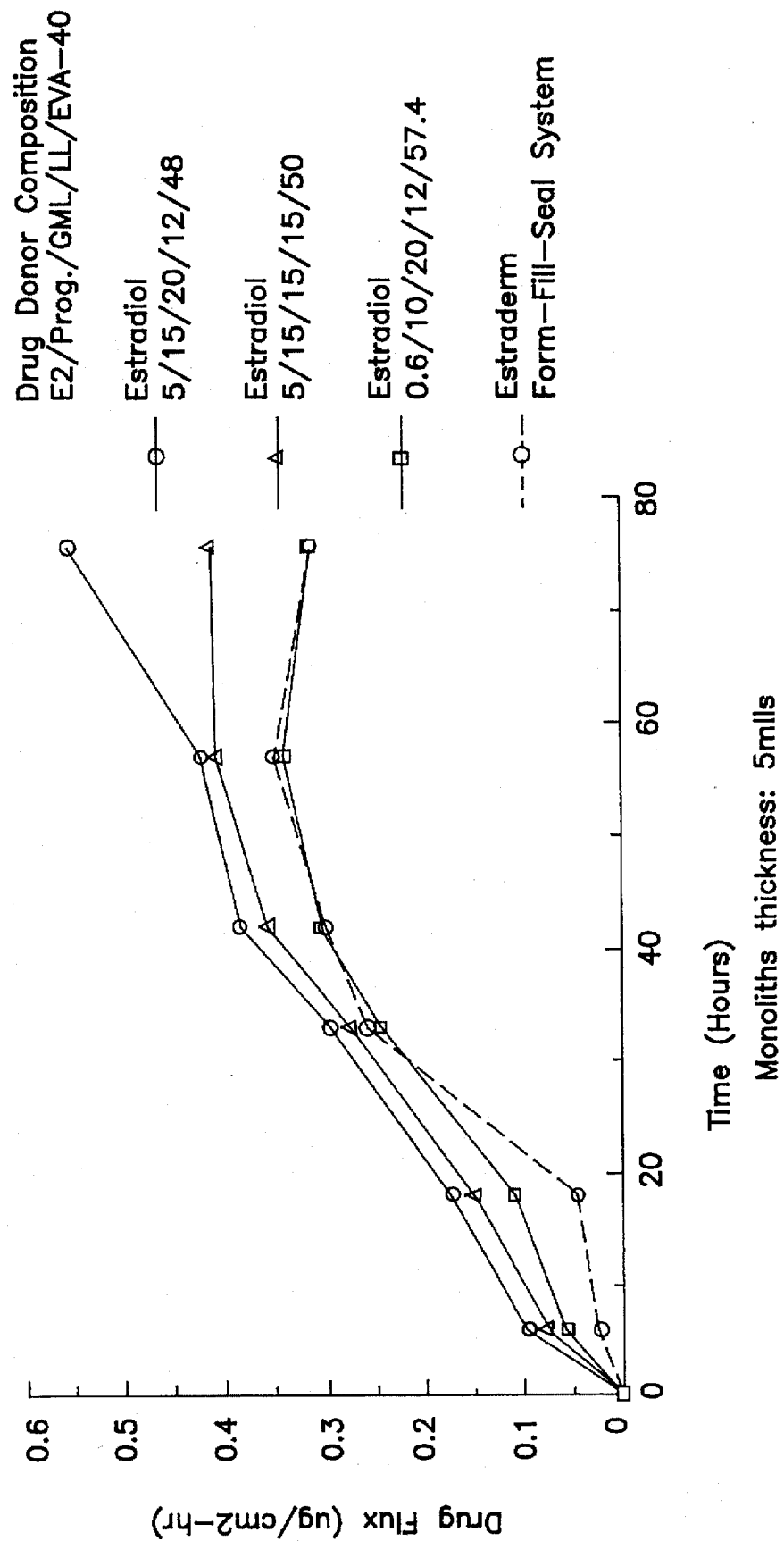
FIG. 5 is a graph of the flux of estradiol through human epidermis at 35° C., in vitro, with glycerol monolaurate and lauryl lactate as permeation enhancers.
Figure 6:
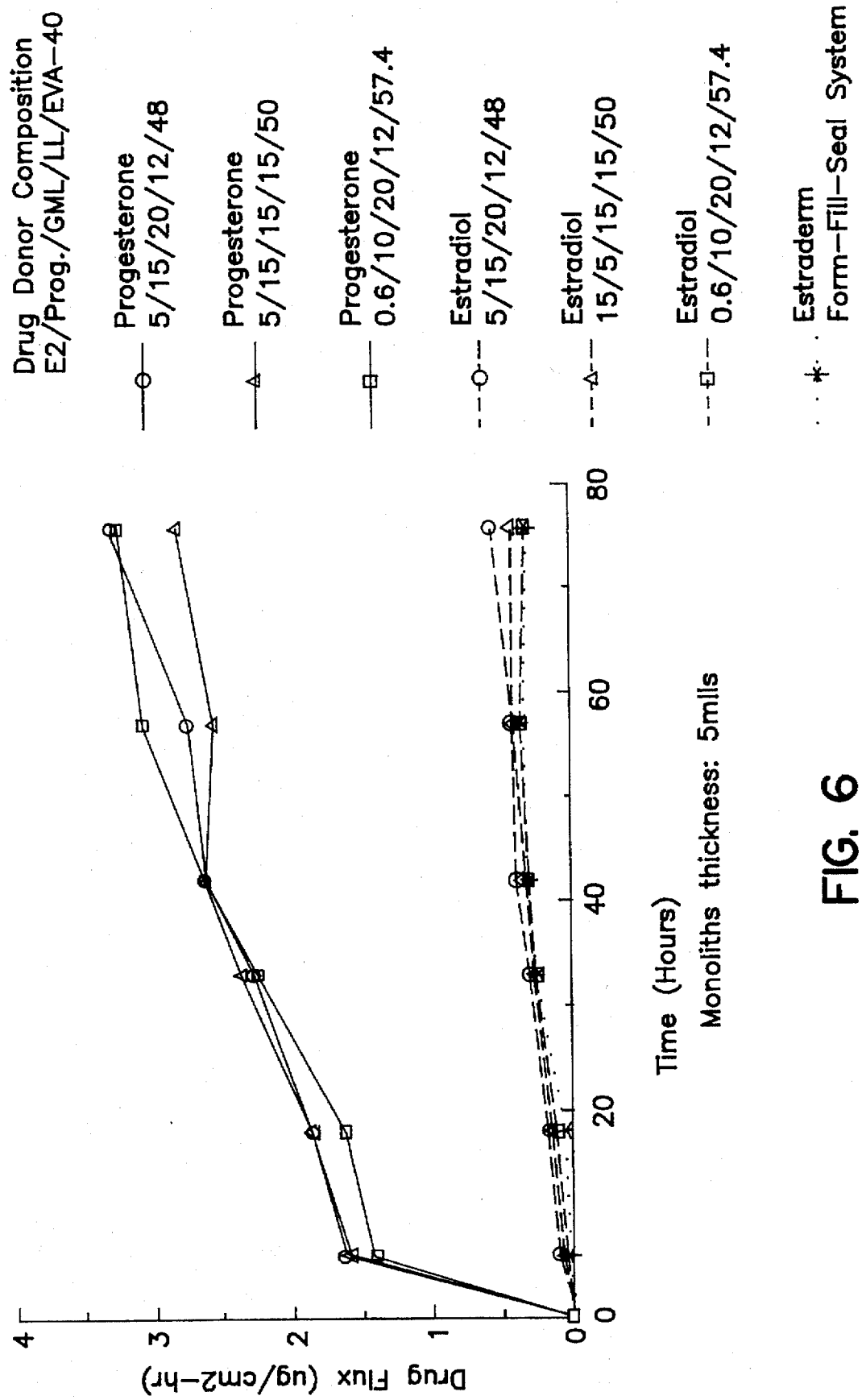
FIG. 6 is a graph of the fluxes of estradiol and progesterone through human epidermis at 35° C., in vitro, with glycerol monolaurate and lauryl lactate as permeation enhancers.
Figure 7:
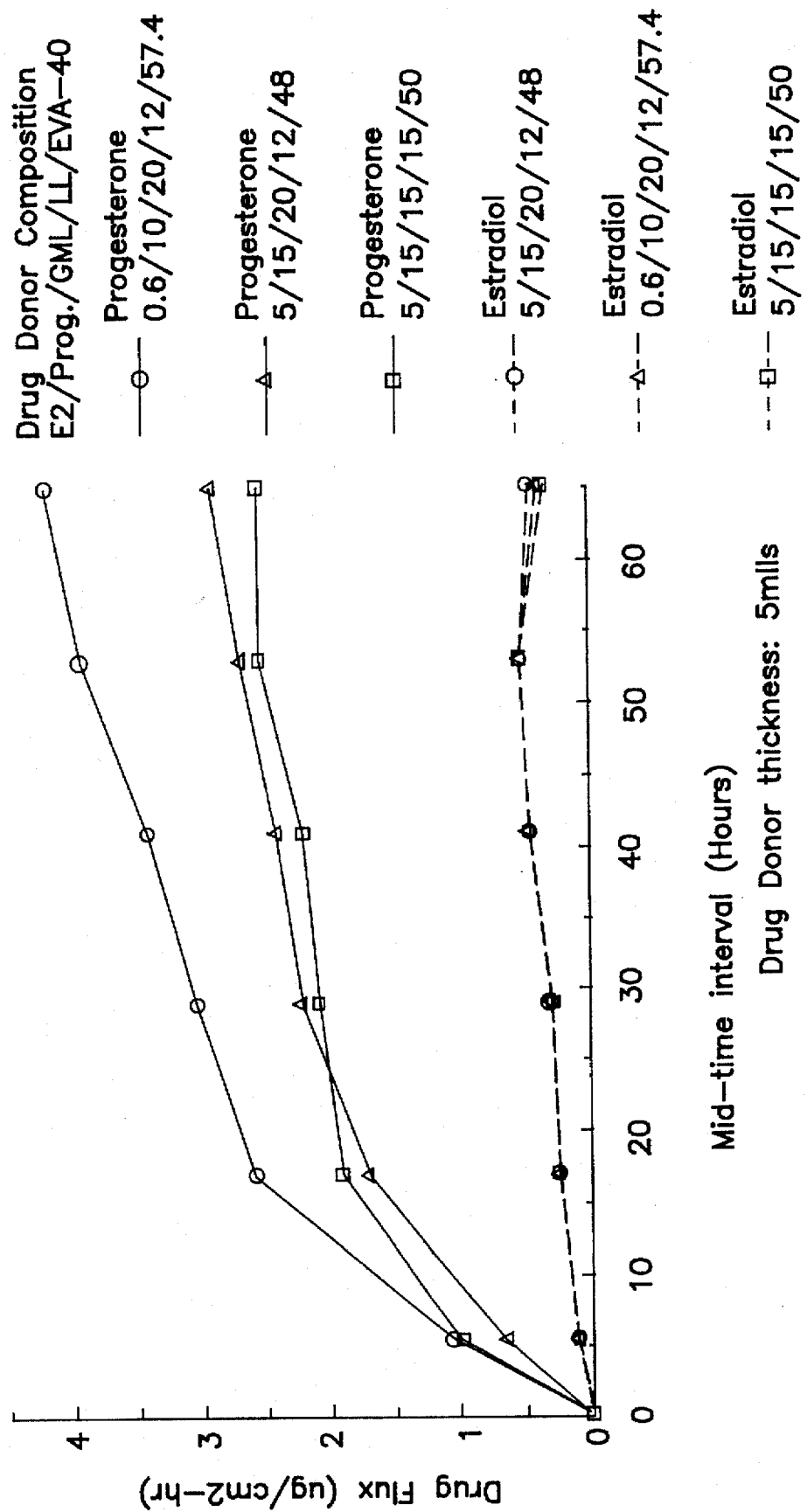
FIG. 7 is a graph of the fluxes of estradiol and progesterone through human epidermis at 35° C., in vitro, with glycerol monolaurate and lauryl lactate as permeation enhancers.

At given time intervals, the entire receptor solution was removed from the cells and replaced with an equal volume of fresh receptor solution previously equilibrated at 35° C. The receptor solutions were stored in capped vials at 4° C. until assayed for estradiol and progesterone concentrations by HPLC. From the drug concentration data, volume of the receptor solutions, the area of permeation and the time interval, the flux of the drug through the epidermis was calculated as follows: (drug concentration×volume of receptor)/(area×$\Delta$time)=flux ($\mu$g/cm$^2$·hr). The fluxes achieved for the different systems are shown in FIGS. 5 to 7.

EXAMPLE 2

The drug/permeation enhancer reservoir was prepared by mixing ethylene vinyl acetate copolymer having a vinyl acetate content of 40 percent ("EVA 40", U.S.I. Chemicals, Illinois) in an internal mixer (Bra Bender type mixer) until the EVA 40 pellets fused. Estradiol and glycerol monolaurate or glycerol monooleate were then added. The mixture was blended for approximately 30 minutes at 40°–45° C. and 26 rpm. After blending, the mixture was calendered at 79°–81° C. to a 5 mil thick film. The compositions of reservoirs are shown in Table 2.

TABLE 2

| Composition of Reservoir |
| --- |
| estradiol/glycerol monolaurate/ EVA 40 (3/30/67) |
| estradiol/glycerol monooleate/EVA 40 (3/30/67) |

Figure 8:
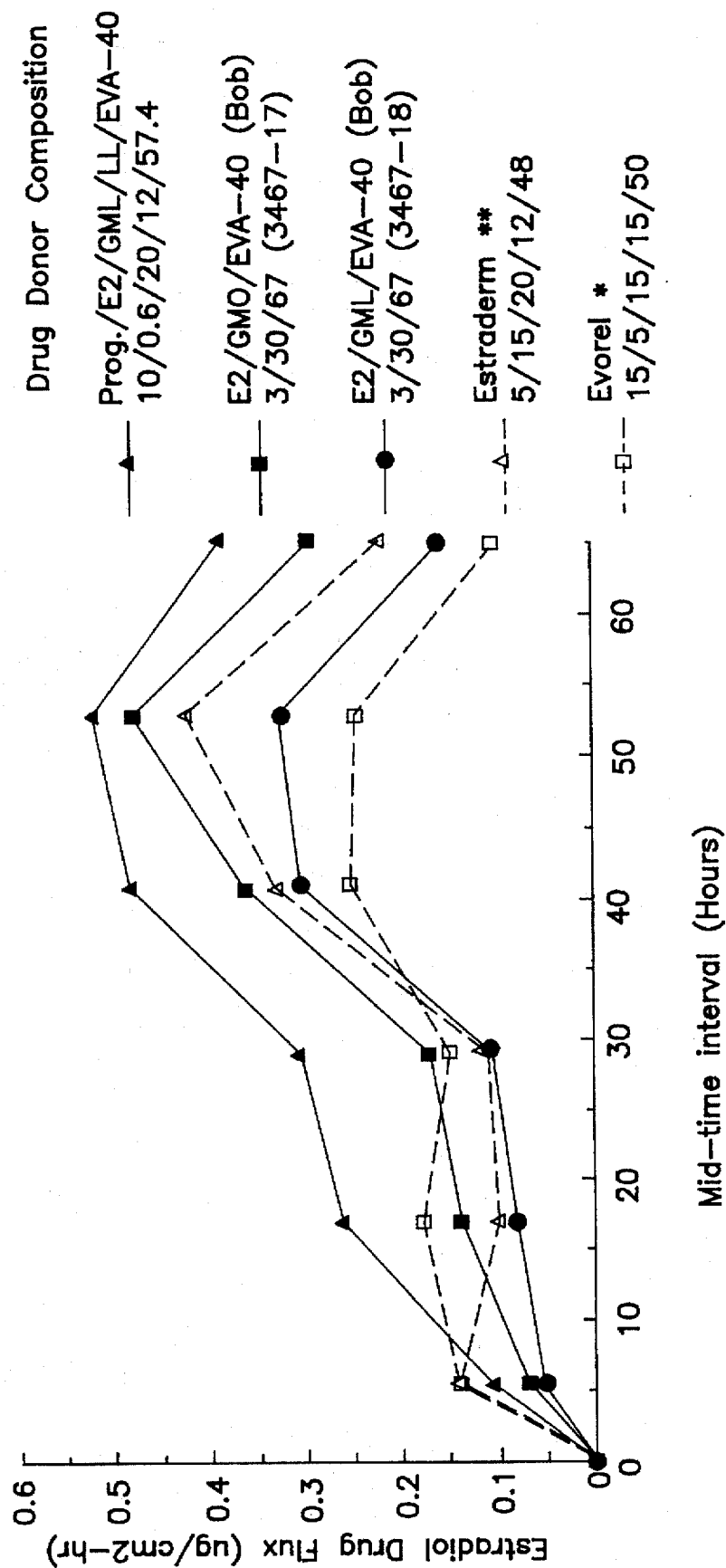
FIG. 8 is a graph of the fluxes of estradiol and progesterone through human epidermis at 35° C., in vitro, with varying weight percents of glycerol monolaurate and lauryl lactate as permeation enhancers.

This film was then laminated to an acrylic contact adhesive (MSP041991P, 3M) on one side and a pigmented Medpar® backing (3M) on the opposite side. The laminate was then cut using a stainless steel punch. The estradiol flux was then determined in the manner disclosed in the previous example. The estradiol flux is shown in FIG. 8.

EXAMPLE 3

The drug/permeation enhancer reservoir was prepared by mixing Gelva 737 (Monsanto, Itasca, Ill.) solution with glycerol monolaurate and lauryl lactate in a jar in a Roto-Torque mixer overnight. The solution was then cast on an FCD-1020 (3M, Minneapolis, Minn.) release liner and evaporated to dryness in the hood at room temperature for 5 days. Progesterone, estradiol, glycerol monolaurate and lauryl lactate were then added and mixed in an internal mixer (Bra Bender type). The mixture was then calendered to a 5 mil thick film. The compositions of the reservoir is given in Table 3.

TABLE 3

| Drug/Permeation Enhancer Reservoir Composition (weight percent) |
| --- |
| Progesterone/estradiol/glycerol monolaurate/lauryl lactate/Gelva 737 (10/0.6/20/12/57.4) |
| Progesterone/estradiol/glycerol monolaurate/lauryl lactate/Gelva 737 (10/0.6/7/10/72.4) |
| Progesterone/estradiol/glycerol monolaurate/lauryl lactate/Gelva 737 (10/0.6/20/10/59.4) |

This film was then laminated to a pigmented Medpar® backing on one side. The film was then cut into circles and taped to prevent edge release.

For each device tested, the adhesive was placed against the stratum corneum side of a disc of human epidermis that had been blotted dry just prior to use. The excess epidermis was wrapped around the device so that none of the device edge was exposed to the receptor solution. The device covered with epidermis was attached to the flat side of the Teflon holder of a release rod using nylon netting and nickel wire. The rods were reciprocated in a fixed volume of receptor solution, ie, water 1% Tween 20 in water, 2% propylene glycol in water or 2% IPA in water. The entire receptor solution was changed at each sampling time. The temperature of the receptor solution in the water bath was maintained at 35° C.

Figure 9:
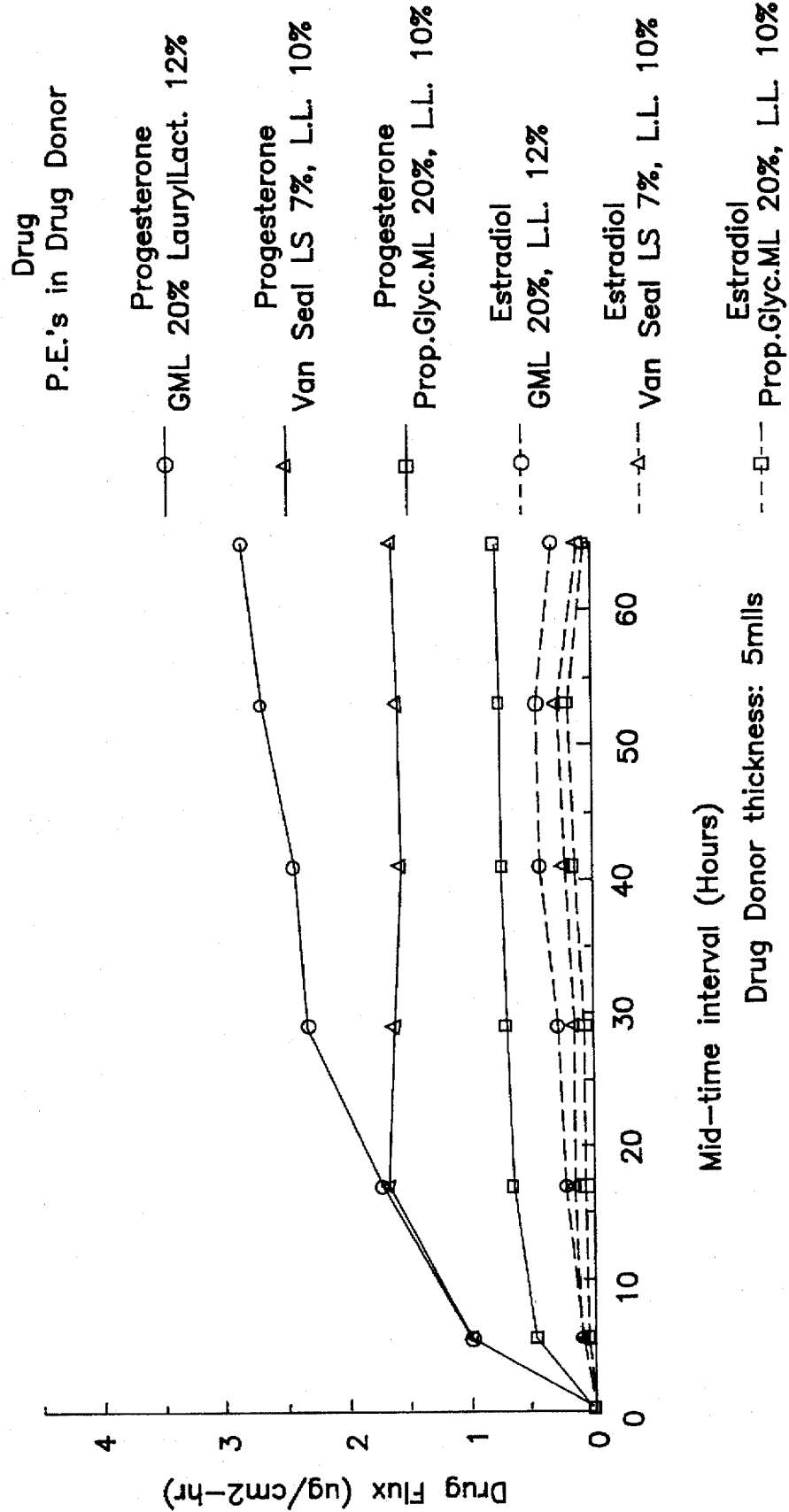
FIG. 9 is a graph of the fluxes of estradiol and progesterone through human epidermis at 35° C., in vitro, with glycerol monolaurate and lauryl lactate as permeation enhancers.

The receptor solutions were stored in capped vials at 4° C. until assayed for estradiol and progesterone content by HPLC. The fluxes achieved for the different systems are shown in FIG. 9.

This invention has been described in detail with particular reference to certain preferred embodiments thereof, but it will be understood that variations and modifications can be effected within the spirit and scope of the invention.

What is claimed is:

1. A composition of matter for application to a body surface or membrane to coadminister an estrogen and progestogen by permeation through the body surface or membrane, the composition comprising, in combination:

(a) the estrogen and progestogen to be administered, in a therapeutically effective amount; and
(b) a permeation-enhancing mixture comprising:
   (i) 20% by weight of a monoglyceride or a mixture of monoglycerides, and
   (ii) 12% by weight of a lactate ester or a mixture of lactate esters.

2. A composition according to claim 1 wherein the lactate ester is lauryl lactate.

3. A composition according to claim 2, wherein the monoglyceride is glycerol monolaurate.

4. A composition according to claim 1 wherein the estrogen is estradiol.

5. A composition according to claim 4 wherein the estradiol comprises from about 0.6 to about 5% by weight of the composition.

6. A composition according to claim 4 or 5 wherein the progestogen is progesterone and comprises from about 10 to about 15% by weight of the composition.

7. A device for the transdermal coadministration, at a therapeutically effective rate, of an estrogen and progestogen, which device comprises:
(a) a reservoir comprising a therapeutically effective amount of an estrogen and progestogen and a skin permeation-enhancing amount of a permeation mixture comprising:
   (i) 20% by weight of a monoglyceride or a mixture of monoglycerides, and
   (ii) 12% by weight of a lactate ester or a mixture of lactate esters;
(b) a backing on the skin-distal surface of the reservoir; and
(c) means for maintaining the reservoir in drug- and permeation enhancing mixture-transmitting relation with the skin.

8. A device for the transdermal coadministration, at a therapeutically effective rate, of an estrogen and progestogen which device comprises:
(a) a first reservoir comprising a therapeutically effective amount of an estrogen and progestogen, and a skin permeation-enhancing amount of a permeation mixture comprising:
   (i) 20% by weight of a monoglyceride or a mixture of monoglycerides, and
   (ii) 12% by weight of a lactate ester or a mixture of lactate esters;
(b) a second reservoir comprising an excess of the permeation enhancing mixture and the estrogen and progestogen at or below saturation;
(c) a rate-controlling membrane between the first reservoir and the second reservoir;
(d) a backing on the skin-distal surface of the second reservoir; and
(e) means for maintaining the first and second reservoirs in drug- and permeation enhancing mixture-transmitting relation with the skin.

9. A device according to claim 7 or 8 wherein the monoglyceride is glycerol monolaurate.

10. A device according to claim 7 or 8 wherein the lactate ester is lauryl lactate.

11. A device according to claim 7 or 8 wherein the estrogen is estradiol.

12. A device according to claim 11 wherein the estradiol comprises about 0.6 to about 5% by weight of the drug containing reservoir.

13. A device according to claim 12 wherein the progestogen is progesterone and comprises about 10 to about 15% by weight of the drug containing reservoir.

14. A device according to claim 7 wherein the means for maintaining the reservoir in relation with the skin comprises an in-line adhesive layer on the skin-proximal surface of the reservoir.

15. A device according to claim 8 wherein the means for maintaining the reservoirs in relation with the skin comprises an in-line adhesive layer on the skin-proximal surface of the first reservoir.

16. A device according to claim 8 wherein the first reservoir also is an adhesive layer which functions as the means for maintaining the reservoirs in relation with the skin.

17. A device according to claim 10, wherein the monoglyceride is glycerol monolaurate.

18. A method for the transdermal coadministration of an estrogen and progestogen, which method comprises:
(a) administering the estrogen and progestogen at a therapeutically effective rate to an area of skin; and
(b) simultaneously administering a permeation enhancing mixture comprising:
   (i) 20% by weight based on the drug and permeation enhancer mixture of a monoglyceride or a mixture of monoglycerides, and
   (ii) 12% by weight based on the drug and permeation enhancer mixture of a lactate ester or a mixture of lactate esters, to the area of skin at a rate which is sufficient to substantially increase the permeability of the area to the drug.

19. A method according to claim 18, wherein the monoglyceride is glycerol monolaurate.

20. A method according to claim 18, wherein the lactate ester is lauryl lactate.

21. A method according to claim 18, wherein the estrogen is estradiol.

22. A method for providing hormone replacement therapy to a woman, the method comprising the steps of:
(a) administering each component of a drug formulation comprised of an estrogen and progestogen at a therapeutically effective rate to an area of the woman's skin;
(b) simultaneously administering a skin permeation enhancing amount of a permeation enhancing mixture comprising:
   (i) 20% by weight of a monoglyceride or a mixture of monoglycerides, and
   (ii) 12% by weight of a lactate ester or a mixture of lactate esters.

23. A method according to claim 22 wherein the monoglyceride is glycerol monolaurate and wherein the lactate ester is lauryl lactate.

24. A method according to claim 22 or 23 wherein the estrogen is estradiol.

25. A method according to claim 18 wherein the monoglyceride is glycerol monolaurate and the lactate ester is lauryl lactate.

26. A method according to claim 22 wherein the monoglyceride is glycerol monolaurate and the lactate ester is lauryl lactate.

27. A device according to claim 13 wherein the monoglyceride is glycerol monolaurate and the lactate ester is lauryl lactate.

28. A method according to claim 18 wherein the progestogen is progesterone.

29. A method according to claim 22 wherein the progestogen is progesterone.

30. A method according to claim 22 wherein the monoglyceride is glycerol monolaurate.

31. A method according to claim 22 wherein the lactate ester is lauryl lactate.

* * * * *